(12) United States Patent
Ginot

(10) Patent No.: US 6,218,116 B1
(45) Date of Patent: Apr. 17, 2001

(54) METHOD AND DEVICE FOR TREATMENT BY COMPLEXING OF A LIQUID MEDIUM

(75) Inventor: Frederic Ginot, Voreppe (FR)

(73) Assignee: Bio Merieux, Marcy l'Etoile (FR)

( * ) Notice: Subject to any disclaimer, the term of this patent is extended or adjusted under 35 U.S.C. 154(b) by 0 days.

(21) Appl. No.: 09/077,161

(22) PCT Filed: Oct. 6, 1997

(86) PCT No.: PCT/FR97/01781

§ 371 Date: Jun. 26, 1998

§ 102(e) Date: Jun. 26, 1998

(87) PCT Pub. No.: WO98/15832

PCT Pub. Date: Apr. 16, 1998

(30) Foreign Application Priority Data

Oct. 4, 1996 (FR) .................................................. 96 12331

(51) Int. Cl.[7] .................................................. C12Q 1/68
(52) U.S. Cl. .................. 435/6; 435/5; 435/6; 435/94; 436/501; 422/55; 422/56; 422/57; 422/58; 422/68.1
(58) Field of Search ..................... 435/6, 5, 94; 436/501; 422/55, 56, 57, 58, 68.1; 374/31

(56) References Cited

U.S. PATENT DOCUMENTS

| | | | |
|---|---|---|---|
| 5,255,976 | * | 10/1993 | Connelly ............................... 374/31 |
| 5,552,270 | * | 9/1996 | Khrapko et al. ......................... 435/6 |
| 5,776,672 | * | 7/1998 | Hashimoto et al. ..................... 435/6 |

FOREIGN PATENT DOCUMENTS

| | | |
|---|---|---|
| 0 535 242 A1 | 3/1992 | (EP) . |
| WO 92/10588 | 6/1992 | (WO) . |
| WO 92 16655 | 10/1992 | (WO) . |

OTHER PUBLICATIONS

Doktycz et al., *Optical Melting of 128 Octamer DNA Duplexes*, vol. 270, No. 15, Issue of Apr. 14, pp. 8439–8445, 1995, pp. 8439–8445.

Breslauer et al., *Predicting DNA duplex stability from the base sequence*, vol. 83, Jun. 1986, pp. 3746–3750.

Schwienhorst et al., *Hamming chromatography*, Molecular Diversity, 1995, pp. 187–192.

* cited by examiner

Primary Examiner—Kenneth R. Horlick
Assistant Examiner—Janell E. Taylor
(74) *Attorney, Agent, or Firm*—Oliff & Berridge, PLC (57) ABSTRACT

A method for determining the presence, in a liquid medium, of a plurality of different nucleic ligands in the free state comprises: (a) providing a support for plural complexing on which are distributed a plurality of immobilizing sites in which are immobilized a plurality of different nucleic anti-ligands; and (b) contacting the liquid medium with the support, whereby the nucleic ligands are paired with the nucleic anti-ligands. The stability of each ligand/anti-ligand complex is dependent upon at least one exogenous parameter, namely temperature, conditioning the support; the immobilizing sites on the support are differentiated, depending on the exogenous parameter, having respectively different values in the sites; and the anti-ligands are distributed among the different immobilizing sites, depending on the optimum values of the exogenous parameter, determining the stability of the different nucleic ligand/anti-ligand complexes respectively. This method may be used for sequencing nucleic acids by hybridization.

19 Claims, 5 Drawing Sheets

METHOD AND DEVICE FOR TREATMENT BY COMPLEXING OF A LIQUID MEDIUM

The present invention relates generally to the treatment by complexing of a liquid medium, comprising one or more components determining the presence, in said liquid medium, of a plurality or multiplicity of different ligands in the free state.

In the present description, and the claims, the following definitions are adopted below.

"Ligand" is understood to mean any entity or molecule, of a chemical, biochemical or biological nature, capable of binding in a specific manner to another entity or molecule, called "anti-ligand", through one or more noncovalent bonds.

Emerging in particular from this definition are different biological or biochemical entities, in particular biopolymers, capable of forming a complex with each other and in a complementary manner:

they represent, for example, a polypeptide, in particular an antibody (ligand) capable of specifically binding to an epitope or antigen (anti-ligand), or conversely they also represent, as shown by way of example in the description below, any nucleic acid or nucleic material capable, in single-stranded form, of binding in a complementary manner to an oligonucleotide or a polynucleotide.

The reaction or equilibrium of a chemical nature, by which the ligand binds, or pairs, or forms a complex with the anti-ligand, will be designated hereinafter by the term "complexing". The product of this reaction or equilibrium will be designated hereinafter by the term "complex". In the case of a nucleic material or macromolecule, the complex will be designated hereinafter by the term "duplex". "Nucleic material" or "nucleic acid" is understood to mean any macromolecule comprising at least one unbranched, linear chain of nucleotides, which are themselves modified or otherwise. Emerging from this definition are, quite obviously, any deoxyribonucleic acid, modified or otherwise, and any ribonucleic acid, modified or otherwise. Such a macromolecule may be single-stranded, or double-stranded, or may have any other secondary or tertiary conformation. In practice, in the description hereinafter and by way of example, this nucleic material will be the one directly subjected to the treatment, or the one from which a liquid medium is obtained, containing the ligand(s), so as to then be treated in accordance with the present invention.

"Oligonucleotide" is understood to mean any polynucleotide, comprising at least five monomers, and preferably at least seven, for example eight monomers, which consist of a natural nucleic acid, or a nucleic acid modified on at least one of its constituent components, namely on the sugar, the nitrogenous base or the phosphate group.

"Support" is understood to mean any substrate at the surface of which anti-ligands may be permanently immobilized or attached, directly or indirectly, both covalently and noncovalently.

The substrate is either self-supporting, for example a sheet of an inert and transparent material, or is itself supported by a rigid base, for example a layer of acrylamide on a glass slide.

"Surface" is understood to mean the surface of the substrate accessible to the anti-ligands, whether it is a solid substrate or a porous substrate, in which case the true surface developed is greater than the apparent surface.

In the description hereinafter and by way of example, the oligonucleotides will constitute the anti-ligands defined above.

The complexing reaction between a nucleic material or a nucleic acid, on the one hand, and a complementary oligonucleotide, on the other, may be designated hereinafter by the term "hybridization".

In accordance with the document WO-92/10558 and WO-93/22680, and according to a so-called "reverse dot-blot" bioassay format, a method and a device are described for treatment by complexing, namely hybridization, of a liquid medium, in the case of a nucleic sample, comprising one or more nucleic components, determining the presence in this liquid medium of a plurality of different nucleic fragments, segments or sequences (ligands) in the free state. The principal application of this treatment is the sequencing, by hybridization, of the nucleic sample according to known principles and methods disclosed in documents (6) and (7).

According to this method:

a) a support for plural complexing, of the biochip type, is provided on which there are distributed a plurality of discrete coupling sites or zones, separated from each other, in which there are immobilized a plurality of oligonucleotides (anti-ligands) which are respectively different and capable of being complexed with the nucleotide sequences complementary to the nucleic fragment(s), respectively;

b) under isothermal conditions from one coupling site to another, the liquid medium, or nucleic sample, is brought into contact with this complexing support, whereby the free nucleotide sequences pair with the fixed oligonucleotides respectively, and are as a result attached to the plural complexing support;

c) a parameter representative of the presence and/or of the quantity of the different complexes or hybrids obtained is observed at the different coupling sites of the plural complexing support, so as to generate signals and/or information which are representative of the presence and/or of the quantity of the different nucleotide sequences in the original liquid medium; preferably, these complexes are observed using labeling of the component(s) of the nucleic sample, or labeling of the different hybrids which are obtained and which are attached to the support.

As stated above, this process works under completely isothermal conditions, that is to say by providing the same hybridization temperature from one coupling site to another, at the time of bringing the liquid medium into contact with the plural complexing support, and/or at the time of washing this support after hybridization.

In accordance with the document EP-0,535,242, a similar method has been described and proposed which also works under isothermal conditions, and according to which at each coupling site, the concentration of corresponding oligonucleotide specific for said site is chosen as a function of the working temperature, so as to promote the stability of the corresponding complex obtained with the complementary nucleotide sequence.

According to this document, this concentration is chosen by observing the percentages of complementary nucleotide sequence eluted at each coupling site, during a washing phase which is performed with a washing liquid whose temperature is varied and which is incorrectly termed heat gradient washing.

The solutions described above are subject to a technical difficulty which is identified in the document WO-92/10588 but which has not been solved. Indeed, at a predetermined hybridization temperature, and for a given length of sequence of the oligonucleotide (anti-ligand), the stability of the complex obtained by hybridization of a nucleic acid probe with its target complementary sequence varies according to this sequence. Thus, two oligonucleotides differing from each other only by one of the nucleotides, namely T in one case and G in the other case, although of the same length and of a similar sequence, do not hybridize their respective complementary nucleic acids with the same stability. In other words, since the stability of the complexes obtained depends on the temperature, the sample nucleic acid should be hybridized with the oligonucleotide probes, carried on the plural complexing support, at a sufficiently cold temperature for the least stable of the possible complexes to form, otherwise false-negatives will be obtained after hybridization, that is to say oligonucleotide probes generating no hybridization signal although their complementary sequence is present in the sample. However, by carrying out the procedure in this manner, there are instances in which oligonucleotide probes form complexes which are sufficiently stable with sequences which are not perfectly complementary; in such a case, false-positives are then obtained, that is to say oligonucleotide probes generating a hybridization signal although their complementary sequences are not present in the nucleic sample.

Since these false-negatives and false-positives consequently introduce errors in the analysis of the nucleic sample, in particular for sequencing by hybridization, they make the technical solution described above often inexploitable.

The object of the present invention is therefore to increase the reliability of a treatment by complexing, in particular hybridization, as described above.

The starting point of the present invention is the observation that the stability or reliability of each ligand/anti-ligand complex depends, directly or indirectly, on at least one exogenous parameter, called hereinafter reference parameter, which conditions the plural complexing support.

"Exogenous parameter" is understood to mean a parameter or a condition which is extrinsic relative to the ligand and/or anti-ligand, that is to say independent of them.

Such an exogenous reference parameter, conditioning or capable of conditioning the plural complexing support, is for example:
  a physical parameter or condition which is applicable to the support, for example the temperature,
  or a chemical, biochemical or biological parameter or condition existing or available at the surface of said support, for example the surface concentration of an anti-anti-ligand capable of pairing with practically all the anti-ligands,
  or alternatively a physicochemical parameter established on the surface of the support, for example its wettability or surface tension relative to the liquid medium.

As a further example, exogenous parameter, in the case of a ligand of the nucleic acid type, and of an anti-ligand of the oligonucleotide type, is understood to mean any parameter or characteristic not belonging to the nucleotide sequences of the nucleic acid and/or of the oligonucleotide, and for example differing from their respective richnesses in any one of the elementary nitrogenous nucleic bases.

The present invention next distinguishes itself by the combination of the following two characteristics:
  on the one hand, in all the support, for example on all of its surface, the coupling sites are differentiated as a function of the exogenous reference parameter, which parameter has values which are respectively different in the different coupling sites
  and the anti-ligands are distributed between the different coupling sites as a function of the predetermined optimum values of the exogenous reference parameter determining in particular the stability of the different ligand/anti-ligand complexes respectively.

Consequently, according to the present invention, each coupling site on the plural complexing support to which a corresponding anti-ligand is immobilized works at an optimum value of the exogenous reference parameter in relation to the stability of the corresponding ligand/anti-ligand complex, it being possible for this optimum value to be different from the optimum value for at least one immediately adjacent coupling site.

By virtue of the invention, a particularly reliable, precise and sensitive mode of plural complexing is obtained which also has a good resolution.

"Coupling" is understood to mean any bonding, covalent or otherwise, which makes it possible to permanently immobilize an anti-ligand at the surface of the support.

The present invention is carried out according to different bioassay formats, for example by direct complexing or by competitive complexing.

The invention is optionally carried out according to a "sandwich" format, according to which the ligand is capable of pairing with the fixed anti-ligand and with a sample in the free state in the liquid medium.

By way of preferred examples, three different practical modalities are selected:
  according to a first modality, the liquid medium is brought into contact with the complexing support by applying the same minimum value of the exogenous reference parameter, this minimum value being sufficient to complex practically all the ligands with the anti-ligands; the support is then washed by applying to the different coupling sites exogenous reference parameter values which are respectively different and predetermined, and this during the sole washing step,
  according to a second modality, this same bringing of the support into contact with the liquid medium is carried out by applying to the different coupling sites first exogenous parameter values which are respectively different and predetermined; the support is then washed by maintaining the different coupling sites at second predetermined values of the exogenous reference parameter which are respectively different; the first values are identical or different from the second values respectively of the exogenous reference parameter,
  according to a third modality, the support is brought into contact with the liquid medium by applying to the different coupling sites exogenous reference parameter values which are respectively different and predetermined, and this during the sole complexing or hybridization step, the hybridized support is then washed with a washing liquid at a relatively cold and constant temperature.

Of course, in a so-called homogeneous type detection mode, a washing step is not essential.

The first modality defined above assumes that at each coupling site, the quantity or concentration of anti-ligand is sufficient to form a complex, on the one hand, with all the ligands which are really complementary to the ligand considered, and, on the other hand, with all the ligands capable of pairing concurrently or in a parasitic manner with this same anti-ligand.

Preferably, a spatial gradation is established on the plural complexing support, in particular in a flat position, for example a gradient of the exogenous reference parameter, in at least one reference direction of the support, for example its width in the case of a rectangular support. This spatial gradation then fixes the position or the arrangement of the different coupling sites, with the distribution of the anti-ligands between the different coupling sites respectively.

As a variant or an addition to the present invention, the coupling sites on the plural complexing supports are differentiated as a function of another exogenous reference parameter, it too having different values in said coupling sites, and, moreover, the anti-ligands are distributed between the different coupling sites, also as a function of predetermined optimum values of the other exogenous reference parameter which also determines the stability of the different ligand/anti-ligand complexes respectively.

Preferably, another exogenous parameter on which the stability of the different ligand/anti-ligand complexes depend is set at a mean value between those of said other parameter which are required for the stability of the different ligand/anti-ligand complexes respectively. By way of example, this other exogenous parameter is the pH or the ionic strength of the liquid medium which is brought into contact with the plural complexing support, a parameter depending on the composition of the hybridization buffer.

The plural complexing support, designed and conditioned according to the invention as regards its different coupling sites, is preferably used for the detection and/or quantification of the ligands.

For this purpose, several modalities are considered:
  a variable representative of the presence and/or of the quantity of the different ligand/anti-ligand complexes is observed in particular by scanning at the different coupling sites of the support in order to obtain signals and/or information which are representative of the presence and/or of the quantity of the different ligands in the original liquid medium
  preferably, the different ligand/anti-ligand complexes are observed using at least any one of the following operations which are well known per se, namely labeling of the component(s) of the liquid medium, and labeling of the different ligand/anti-ligand complexes attached to the support.

Conventionally, the liquid medium brought into contact with the support is obtained from a sample, for example a biological sample or material, subjected to analysis and containing one or more different entities, and this according to two modalities:
  either the sample is treated directly according to the method defined above, in particular directly by bringing into direct contact with the plural complexing support
  or the sample is subjected to at least one preliminary operation chosen so as to obtain one or more components in the liquid medium treated which are identical to or derived directly from the different entities respectively, and which are representative of the latter.

Still conventionally, the complexing support onto which the different ligands are attached is optionally subjected to at least one subsequent operation, such as washing, chosen in order to separate from said support the component(s) which have not been complexed, or those which were complexed with the anti-ligands in an unstable manner, and/or to elute or release the different ligands, differentially or otherwise.

A preferred but nonexclusive field of application of the present invention relates to the treatment and analysis of nucleic products or compounds. In this case, the ligand is a nucleic acid which comprises a free target nucleotide sequence, in particular in single-stranded form, which is accessible to hybridization with another fixed or attached complementary probe nucleotide sequence comprised by a corresponding anti-ligand.

Still for a nucleic material, preferably, the liquid medium comprises a single component, namely a nucleic acid, comprising or exhibiting several ligands which are respectively different, namely several regions or segments for hybridization, whereby the same component is paired with the different anti-ligands, namely oligonucleotides respectively. Consequently, in this case, the succession of nucleotides of at least one nucleic acid strand determines a plurality of hybridization regions, and therefore of ligands, according to the target nucleotide sequences, which are respectively complementary to the probe nucleotide sequences of the anti-ligands.

The treatments according to the invention, which are applied to nucleotide or nucleic products or compounds, are used for example in at least any one of the following applications, namely sequencing by hybridization of the nucleic component of the liquid medium, resequencing of this same nucleic component, mapping of a nucleic material, analysis and identification of a nucleic material or sample, typing of a nucleic material, screening of a nucleic material, genetic analysis (cf. for example bibliographic reference 8), detection of a bacterial or viral pathogenic agent.

One application of the invention is the sequencing of a nucleic material by hybridization, in particular by determining the overlapping sequences of this material. The principles of this sequencing and of its modalities have been described in publications (6) and (7), the contents of which are incorporated by reference into the present description, where necessary. The analysis and processing of the information thus obtained in order to reconstruct the nucleotide sequence of a nucleic material has been described in publications (9) and (10).

Another application of the invention is the identification of microorganisms or of genes associated with a microorganism by determining a hybridization profile, without obligatory reconstruction of sequences.

For all these applications, the liquid medium is obtained from a nucleic sample comprising one and the same nucleic fragment, or several different nucleic fragments. And the nucleic sample is optionally subjected to at least one preliminary operation chosen from the following operations, namely denaturation, lysis, fragmentation, cloning and amplification.

Two different cases of treatment according to the invention should be considered:
  in a first case, the liquid medium comprises several different components comprising ligands which are respectively different, whereby said different components are attached and separated from each other, and so to speak resolved on the plural complexing support; this modality is carried out in at least any one of the following applications, namely identification, quantification, separation and fractionation of the different components,
  in another case, the liquid medium comprises a single component, itself comprising or exhibiting several ligands which are respectively different, whereby the same component is paired with the different ligands respectively.

A device for treatment in accordance with the invention comprises:
  a plural complexing support on which there are arranged or distributed, for example in matrix form, a plurality of coupling sites, separated from each other, in which there are immobilized a plurality of anti-ligands which are respectively different and which are capable of being complexed with said ligands respectively, a means for bringing the liquid medium into contact with the support, designed so as to pair said ligands with said anti-ligands respectively and to attach them to said support.

This device is characterized in that, on the one hand, it comprises, in addition, means for differentiating the coupling sites on the support, as a function of the exogenous reference parameter, with values of said parameter which are respectively different in said sites, and, on the other hand, the anti-ligands are distributed on the support, between the different coupling sites, as a function of the predetermined optimum values of the exogenous reference parameter determining the stability of the different ligand/anti-ligand complexes respectively.

Preferably, but not exclusively, the exogenous reference parameter selected being the temperature, the differentiating means are designed to graduate the temperature according to at least one reference direction, for example according to a temperature gradient. In this case, preferably, the device comprises a cold source and a hot source between which said support extends in the reference direction.

By way of example, such a device comprises one or more sensors, combined with the different coupling sites of the support respectively, detecting at least one observed variable representative of the presence and/or of the quantity of ligand/anti-ligand complex at each coupling site, and delivering one or more measuring signals or corresponding information.

By way of example, the device comprises a single sensor, itself composed of multiple elementary sensors, for example a CDD camera, or a single sensor scanning the surface of the plural complexing support.

For example, for the analysis or sequencing of a nucleic material, this same device comprises or is combined with a unit for processing the signals delivered by the different sensors based on predetermined mathematical and/or logical operations, so as to obtain information characterizing the component(s) in the liquid medium.

By way of example, the observed variable representative of the presence and/or of the quantity of ligand/anti-ligand complex is the light absorbance or the intensity of emitted or re-emitted light (fluorescence or luminescence for example), the intensity of an ionizing radiation, or any other physical, optical, electrical or dielectric or electrochemical property of the different ligand/anti-ligand complexes, for example light diffraction, nuclear magnetic resonance, contact angle variation, electrical conductivity, voltametry, amperometry, impedance measurement.

By way of embodiment, the plural complexing support comprises one of the following inert materials, glass, a vitreous material, a porous, inorganic or amorphous material, and a plastic material.

When a biochip is used, this support and the coupling sites are obtained according to traditional photolithographic techniques (cf. publication No. 11).

The present invention is now described by way of example, with reference to the treatment of a nucleic acid or material according to the experimental protocol detailed hereinafter and referring to the accompanying drawing in which.

in a manner similar to FIGS. 1a to 1d.

EXPERIMENTAL PROTOCOL

According to the following plan:
I—Demonstration of the problem forming the basis of the present invention
   1.1 Choice of the oligonucleotides (anti-ligands)
   1.2 Synthesis of the oligonucleotides
   1.3 Method of grafting the oligonucleotides
   1.4 Hybridizations and visualization of the fluorescence of the complexes
   1.5 Results of hybridization at isothermal temperatures
II—Resolution of the problem with the aid of a plural complexing support whose coupling sites are differentiated based on a heat gradient
   2.1 Description of the device according to the invention allowing the application of a heat gradient
   2.2 Positioning of the oligonucleotides at their predetermined optimum hybridization temperature
   2.3 Results of hybridization in a heat gradient, according to the invention
   2.4. Extrapolation of the operation of a "biochip" to universal oligonucleotides
I—Demonstration of the problem forming the basis of the present invention
   1.1—Choice of the oligonucleotides (anti-ligands)

To show the difficulties encountered for a traditional hybridization of nucleic acids (ligands) with oligonucleotides immobilized at the surface of a solid support, model oligonucleotides which are representative in this type of analysis were chosen.

The length of the oligonucleotides chosen is 8 bases: it is a length which is commonly accepted for an application of the type involving sequencing by hybridization. (bibliographic references 1 and 2).

3 base sequences, noted B, D and J, were chosen. They are characterized by the differences in the stability of the corresponding double-stranded DNAs. Sequence B, rich in A and T nucleotides, will form a relatively unstable duplex with its complementary sequence. On the other hand, sequence J, rich in C and G nucleotides, will form a relatively stable duplex with its complementary sequence. Sequence D, containing as many A and T nucleotides as C and G nucleotides, will form a duplex of intermediate stability with its complementary sequence. It is possible to roughly predict the relative stabilities of the double-stranded oligodeoxyribonucleotides using the nearest neighbor model of Breslauer et al. (cf. bibliographic reference 3). This model makes it possible to calculate, for each duplex and at any temperature, the free binding energy as a function of its sequence.

From these three base sequences (noted B, D and J, see below), seven other sequences were determined, which correspond to single variations of the B, D or J sequences.

It is these 10 oligonucleotides which were immobilized on a solid plural complexing support. They contain a biotin group at their 5' end, which is necessary for their immobilization (see §1.3 hereinafter). In the table below, the three base sequences are written in bold. In the "remark" section, the suffix "c" designates the complementary sequence.

| Name | Sequence | Remark |
|------|----------|--------|
| bA | 5'b-ACTGATGA3' | Single external mismatch with Dc |
| bB | 5'b-AATCATTA3' | rich in AT |
| bC | 5'b-GAGCATTA3' | Double internal mismatch with Bc |
| bD | 5'b-ACTGATGC3' | 50% AT. 50% GC. |
| bE | 5'b-ACTCATGC3' | Single internal mismatch with Dc |
| bF | 5'b-AAGCATTA3' | Single internal mismatch with Bc |
| bG | 5'b-GCTGATGC3' | Single external mismatch with Dc or double external mismatch with Ac |
| bH | 5'b-GCACCGTC3' | Single internal mismatch with Jc |
| bI | 5'b-ACGCCGTC3' | Single external mismatch with Jc |
| bJ | p b 5'b-GCGCCGTC3' | rich in GC |

6 fluorescent oligonucleotides (labeled ligands) were hybridized with these immobilized oligonucleotides. They are oligonucleotides which are complementary to the 3 base sequences and to their variants which differ in a terminal nucleotide. They contain a fluorescein at their 5' end.

| Name | Sequence | Remark |
|------|----------|--------|
| fAc | 5'F-TCATCAGT.3' | Complementary to bA |
| fBc | 5'F-TAATGATT3' | Complementary to bB |
| fDc | 5'F-GCATCAGT3' | Complementary to bD |
| fGc | 5'F-GCATCAGC3' | Complementary to bG |

-continued

| Name | Sequence | Remark |
|------|----------|--------|
| fIc | 5'F-GACGGCGT3' | Complementary to bI |
| fJc | 5'F-GACGGCGC3' | Complementary to bJ |

1.2—Synthesis of the oligonucleotides

The biotin- and fluorescein-labeled oligonucleotides were obtained after coupling the activated biotin and fluorescein derivatives with the oligonucleotide sequences functionalized by an amine-containing arm —$(CH_2)_6$—$NH_2$— at the 5' position.

1.2.1—Synthesis of the oligonucleotides

The amine-containing oligonucleotides were synthesized on an ABI 394 apparatus (Applied Biosystems, Forster City, Calif.) according to the phosphoramidite method using the protocol given by the manufacturer. All the reagents, including the phosphoramidite precursor of the amine-containing arm, are provided by Applied Biosystems. After cleavage from the support and deprotection, the oligonucleotide sequences are abovementioned [sic] by addition of a sodium acetate solution (3 M) and of cold ethanol (−20° C.)

1.2.2—Synthesis of the conjugate oligonucleotide-biotin in 5'

The amine-containing oligonucleotide is dried and then solubilized in a 0.2 M sodium carbonate buffer solution containing 0.15 M NaCl (pH 8.8). A biotin solution (biotinoylamidocaproic acid N-hydroxy-succinimide ester, Boehringer) in DMF (5 mg/l) is then added. After incubating for 2 hours at 37° C., the reaction is blocked by addition of 10 microliters of an ammonium chloride solution (1 M). The biotinylated oligonucleotide is then precipitated at −80° C. in ethanol and sodium acetate (3 M), solubilized in pure water and then purified by reversed-phase HPLC. Its concentration was determined by UV measurement at 260 nm.

1.2.3—Synthesis of the conjugate oligonucleotide-fluorescein in 5'

The amine-containing oligonucleotide is dried and then solubilized in a 0.2 M sodium carbonate buffer solution containing 0.15 M NaCl (pH 8.8). A solution of fluorescein isothiocyanate (Aldrich) in DMF (12.5 mg/l) is then added. After incubating for 2 hours at 55° C., the reaction is blocked by addition of 25 microliters of an ammonium chloride solution (1 M). The fluorescent oligonucleotide is then precipitated and purified as indicated above. Its concentration was determined by UV measurement at 260 nm.

The purity of the different conjugates is checked by reversed-phase HPLC.

1.3—Method of grafting (immobilization) of the oligonucleotides (anti-ligands)

The solid support selected for the experiments is a microscope slide. It is a common support for this type of analysis. The slides used have the dimensions 75×25×1 mm. The method of immobilizing the oligonucleotides used is composed of techniques commonly used in glass surface derivatization and in molecular biology.

The first step consists in grafting amine groups onto the glass surface by means of silanization. In the second step, the surface is activated by means of a coupling agent which reacts strongly with the amines. In a third step, avidin is covalently grafted onto the activated surface by the reaction of the primary amines of its amino acids with the coupling agent. Finally, in a final step, the biotinilated oligonucleotides are immobilized onto the surface by means of the strong binding of the biotin by avidin.

This method ensures attachment of the oligonucleotides onto the glass surface by their 5' end.

Detailed protocol:
1. Wash the glass slides with sulfochromic acid (Prolabo) diluted one tenth, rinse them with water, dry them at 80° C. for 15 minutes.
2. Immerse the slides in a toluene solution containing 1% (vol/vol) of 3-aminopropyldimethylethoxysilane (company ABCR). Allow to incubate for 20 minutes at room temperature.
3. Rinse the slides twice with ethanol and dry them for 15 min at 80° C.
4. Immerse the slides in dimethylformamide containing 10% (vol/vol) of pyridine, and 0.2% (w/vol) of 1,4-phenylene diisothiocyanate (Aldrich).
Allow to incubate for 1 h at room temperature.
5. Rinse the slides in methanol, and then acetone, and dry them for 15 min at 80° C.
6. Place 2 ul drops of avidin in solution at the desired points. The avidin solution is composed of 10 mM Tris-HCl pH 8; 1 mM EDTA; avidin 1 mg/ml (Sigma). Allow to incubate for 20 to 30 minutes at room temperature.
7. Take up the drops of avidin with a pipette.
8. Rinse the avidin deposits with a 1 M NACl solution, still by depositing 2 $\mu$l drops and by taking them up with a pipette.
9. Deposit the 2 $\mu$l drops of biotinilated oligonucleotides (5 $\mu$M) at the same points. Allow to incubate for 30 minutes at room temperature. Remove the drops with a pipette. The oligonucleotides are diluted in 10 mM Tris-HCl, pH 8; 1 mM EDTA; 1 M NaCl.
10. Immerse the slides in a solution containing 1% ammonium hydroxide (vol/vol) and 1 M NaCl. Leave them for 10 minutes at room temperature.
11. Rinse the slides with water and dry them in ambient air.

The slides are then ready for the hybridization or complexing.

To determine the coupling sites and to position the oligonucleotides precisely on the glass slides, steps 6 to 9 were automated by means of a Gilson robot, model 222. This robot is composed of a cartesian robot arm provided with a needle connected to a diluter. This assembly allows the deposition and the taking up of drops in a precise and reproducible manner.

1.4—Hybridizations and visualization of the fluorescence (variable characterizing the presence and/or the quantity of complex)

The fluorescent oligonucleotides were hybridized onto the surface carrying the immobilized oligonucleotides at a concentration of $10^{-7}$ M in the following buffer: 50 mM Tris-Cl pH 8; 4.5 M TMACl; 2 mM EDTA; 0.01% sarcosine. This buffer is obtained from the bibliographic reference 4.

The hybridization volume is 150 $\mu$l. This volume corresponds to a liquid film of about 0.1 mm thick when 24×50 mm glass coverslips are used.

The duration of hybridization is 1 h.

The isothermal hybridizations were performed between the slide and the glass coverslip, in a tank or a water bath providing the desired temperature.

For the hybridizations according to the invention with heat gradient (see hereinafter), the hybridization solution (liquid medium) is deposited directly on the block of metal supporting the gradient, and the slide carrying the oligonucleotides was applied over, being careful to avoid the formation of bubbles.

The visualization or observation of the hybridizations (complexings) was made by fluorescence, by means of a FluorImager apparatus from the company Molecular Dynamics (Sunnyvale, California, USA). This apparatus scans the surface to be observed by illuminating it point by point, and coupling site by coupling site, by means of an argon laser beam (excitation at 488 nm), and collects the light re-emitted, observed and detected by means of a bundle of optical fibers. A high-baut [sic] filter at 515 nm is included in a non-removable manner in The [sic] apparatus. It is possible to add additional filters to better select as regards wavelength the light collected and observed.

For the observations, an interference filter 530±30 nm was added and the photomultiplier in the apparatus was set at 920 volts. The size of the pixel of the resultant impage [sic] is a 200×200 $\mu$m square. And a coupling site consists of a disk of about 2 mm in diameter, which represents a final image of each site of the order of about ten pixels.

The oligonucleotides (anti-ligands) have a short length, and rapid dissociation of the DNA duplexes takes place at room temperature for the sequences having the lowest stabilities (sequences A and B). Consequently, the following method was developed in order to reliably observe the hybridizations:

1. Rapidly immerse the slides in a hybridization buffer cooled to −20° C. Stir.
2. Rapidly immerse the slides in 20× SSC (commercial reference of the company Ambesco, Solon, Ohio, USA) cooled to −9° C. Stir.

These two steps should take 10 to 15 seconds maximum.

3. Rapidly immerse the slides in hybridization buffer cooled to −20° C. There is no dissociation of the duplex (complex) at this temperature and in this buffer. This buffer should be degassed.
4. Remove the slides from the solution comprising the oligonucleotides of the targets (ligands). Place a previously cooled glass coverslip on top. Rapidly wipe the bottom of the slide.
5. Immediately visualize and observe with the FluorImager apparatus.

The quantification of the hybridizations was carried out by means of the ImageQuant software provided by the company Molecular Dynamics with the FluorImager apparatus.

The protocols described above ensure a coefficient of variation of the hybridization signals of 25% for duplicates carried on the same slide.

1.5—Results of hybridization at isothermal temperature

Slides carrying the 10 oligonucleotides (anti-ligands) bA, bB, bC, bD, bE, bF, bG, bH, bI, bJ were produced and were hybridized at 4° C. with a mixture of the three fluorescent oligonucleotides (ligands) fBc, fDc and fJc, each at the initial concentration of $10^{-7}$M.

The quantitative results of these hybridizations are summarized in Table 1.

This involves the mean of one experiment, in duplicate, and the hybridization signals were expressed as a function of the duplex signal bJ:FJc.

From the values in Table 1, the difference in intensity of the strong and very weak hybridization signals is about 15 times. A non-delectable [sic] hybridization is at least 20 times weaker than a strong hybridization.

As expected, the hybridizations obtained with the oligonucleotides bB, bD and bJ are strong since the free oligonucleotides in solution were their respective complementary strands.

The hybridizations obtained with bC, bE, bF and bH are very weak and non-detectable, which means that the internal mismatches are easily distinguished from the perfect pairings.

On the other hand, the same is not true of the external mismatches. Indeed, while bA generates a relatively weak hybridization signal, the same is not true of bG and bI which generate hybridization signals which are as strong as those for the perfect pairings. The external mismatch formed by the duplex bA:fDc is therefore correctly differentiated, but the external mismatches which the duplexes bG:fDc and bI:fjc form are not.

Under these experimental conditions, it can therefore be seen that it is not possible to finely analyze an unknown sample (liquid medium). Had the above hybridization been carried out with an unknown sample, the oligonucleotides bB, bD, bG, bI and bJ would have been determined as hybridizing with the sample, which represents a false positive level of 40%.

To improve discrimination for the external mismatches, it is possible to think of increasing the hybridization temperature. To explore this solution, the six oligonucleotides bA, bB. bD, bG, bI and bJ were immobilized on a slide, and hybridized with the oligonucleotides fBc, fDc and fic. at different temperatures 4, 10, 20, 25, 30 and 37° C. FIG. 1 represents the hybridization results obtained for the temperatures from 4 to 25° C. They are mean values obtained on 16 to 42 determinations. The results are expressed as relative light intensity for the hybridization bJ:fjc, because this duplex appears to be the most stable. Of course, the absolute intensity of the hybridization signal for this duplex decreases when the temperature increases.

FIG. 1 shows that at 10° C., the profile of the hybridizations is similar to that obtained with hybridizations at 4° C. On the other hand, certain changes take place at 20 and 25° C. The external mismatch bG-fDc becomes markedly weaker than the perfect pairing bI:fJc. Likewise, the external mismatch bI:fjc becomes significantly weaker than the perfect pairing bJ:fjc, although the difference is a little low for a perfect discrimination during a single hybridization. However, the perfect pairing bB:fBc also decreases in intensity and generates a weaker signal than that of the mismatched duplex bI:fjc. Consequently, it is not possible to choose a hybridization intensity threshold which separates without error the perfectly paired duplexes from the mismatched duplexes. For example, if it is chosen to hybridize at 25° C. with a threshold of 0.5, the oligonucleotide bB will be declared negative, and the oligonucleotide bI will be declared positive. The final result will therefore comprise a false positive and a false negative. If a hybridization at 20° C. with a threshold of 0.4 is then chosen, the oligonucleotide bB will be indeed declared positive, but also the oligonucleotide bI, as well as, sometimes, the oligonucleotide bG, according to experimental variations.

II—Solution according to the invention with a heat gradient 2.1—Description of the assembly allowing the application of a heat gradient To solve the problem of discriminating between the external mismatches disclosed above, a treatment device was designed and developed which is capable of establishing a heat gradient at the surface of the glass slide carrying the immobilized oligonucleotides and constituting a plural complexing support.

This device meets the following specifications:
a temperature gradient of IOOC in the useful or working zone 1 cm long
knowledge of the temperature of the slide substrate at every point within 0.1° C.
reproducibility of the temperatures of the slide substrate from one test to another: 0.1° C., within 0.1 mm; the room temperature should be able to vary freely from 20 to 25° C.
ease of installation and removal of the glass slide carrying the oligonucleotides.

Figure 1A:
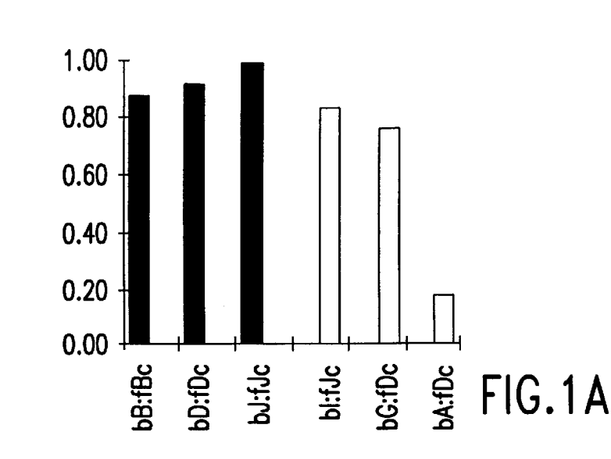
FIGS. 1a to 1d represent the result of isothermal hybridizations at 4° C., 10° C., 20° C. and 25° C. respectively, for oligonucleotides and nucleic fragments identified in abbreviated form on the x-axes; the relative values of the observed variable, namely the light re-emitted by fluorescence of the different complexes obtained, are plotted on the y-axes; the solid bars represent perfect pairings, and the open bars represent external mismatches.
Figure 1B:
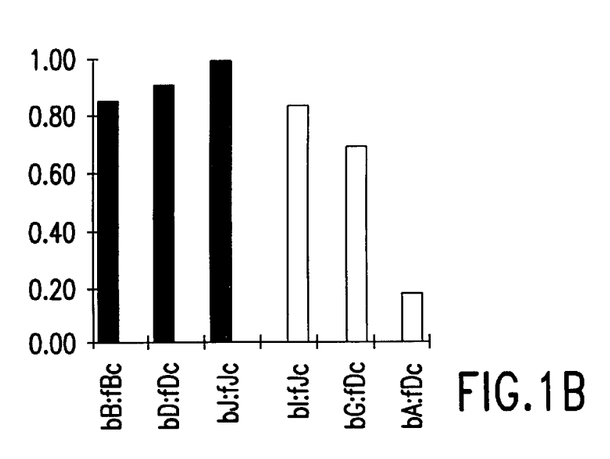
Figure 1C:
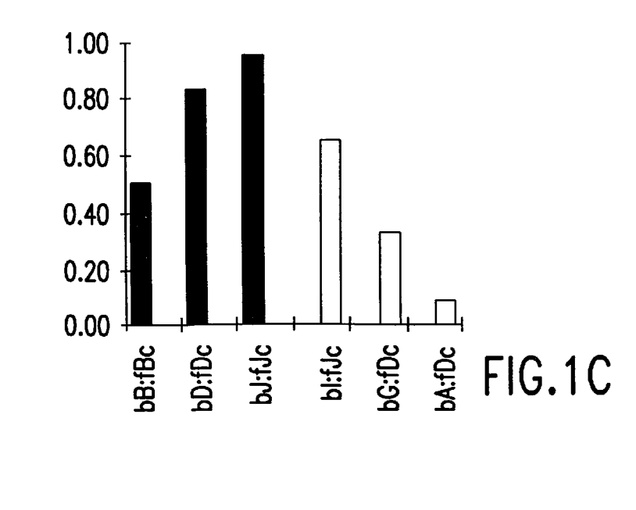
Figure 1D:
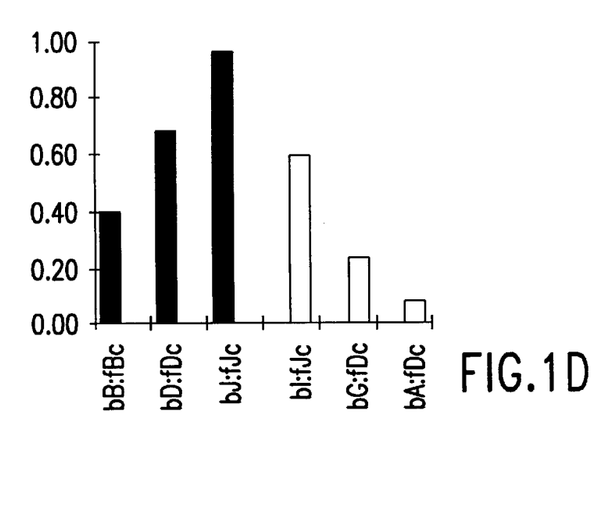
Figures 2, 3:
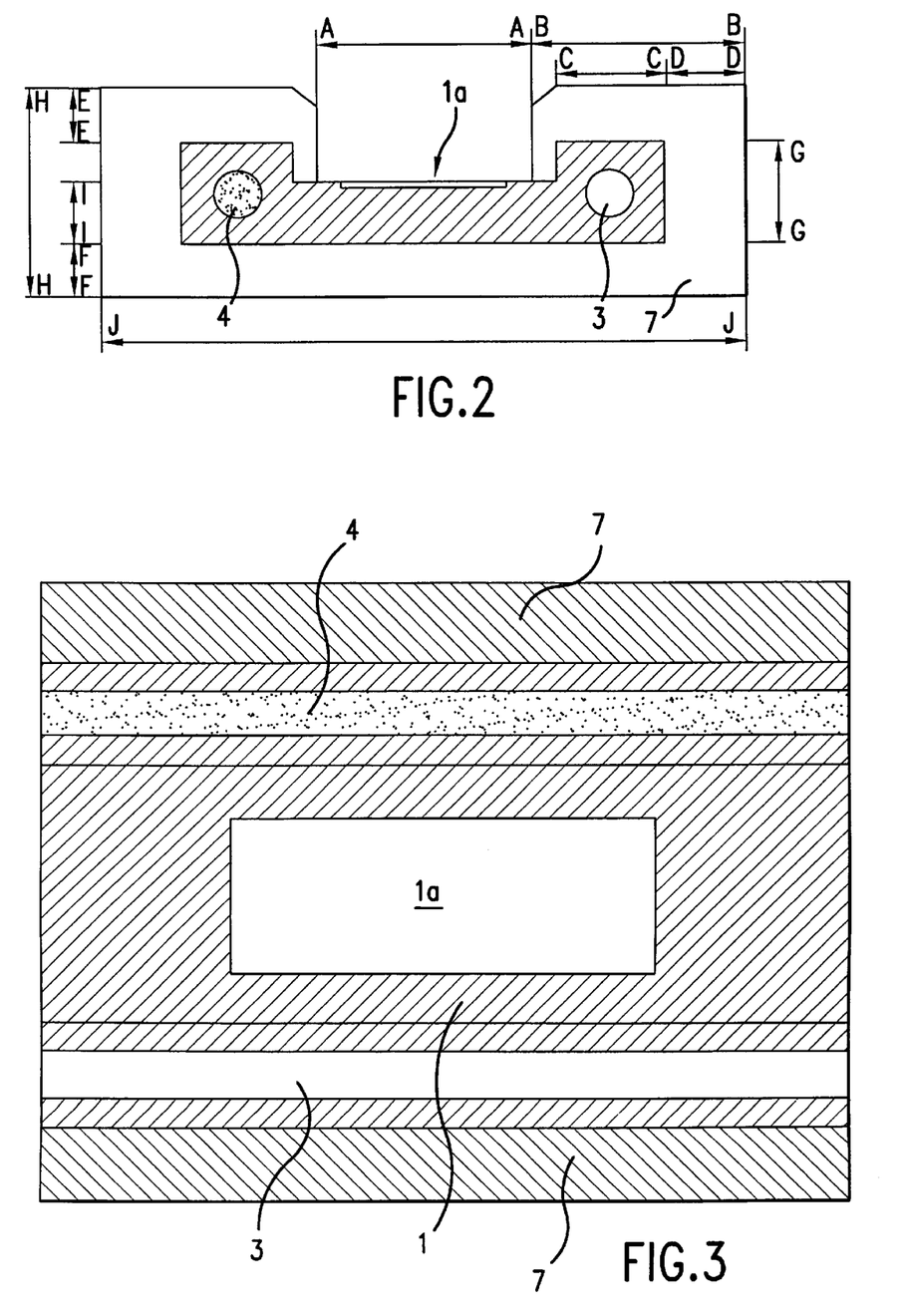
FIG. 2 schematically represents a cross-sectional view of a device for treatment in accordance with the invention.
FIG. 3 schematically represents a top view of the device represented in FIG. 2.

The simplest way of establishing a heat gradient at the surface of a substrate is to connect the ends of this substrate to a cold source 3 and to a hot source 4 respectively. A heat gradient is then established between the two sources. If the substrate is of a constant thickness, the temperature gradient is constant, that is to say that the temperature varies linearly on the substrate as a function of the distance along it.

From a practical point of view, it is necessary that the glass slide 2 on which the oligonucleotides are immobilized is easily replaceable from one test to another, and that there is no difference in heat exchanges between the different tests. That is why the heat gradient was not established directly in the glass slide but in a metal block 1 at the surface of which a small cavity 1a has been dug out. The glass slide 2 is placed in this cavity, the side carrying the immobilized oligonucleotides facing downward. Between the metal block 1 and the glass slide 2 supported by the wedges 11 is the hybridization solution 5 (cf. FIG. 4), or liquid medium.

Figure 4:
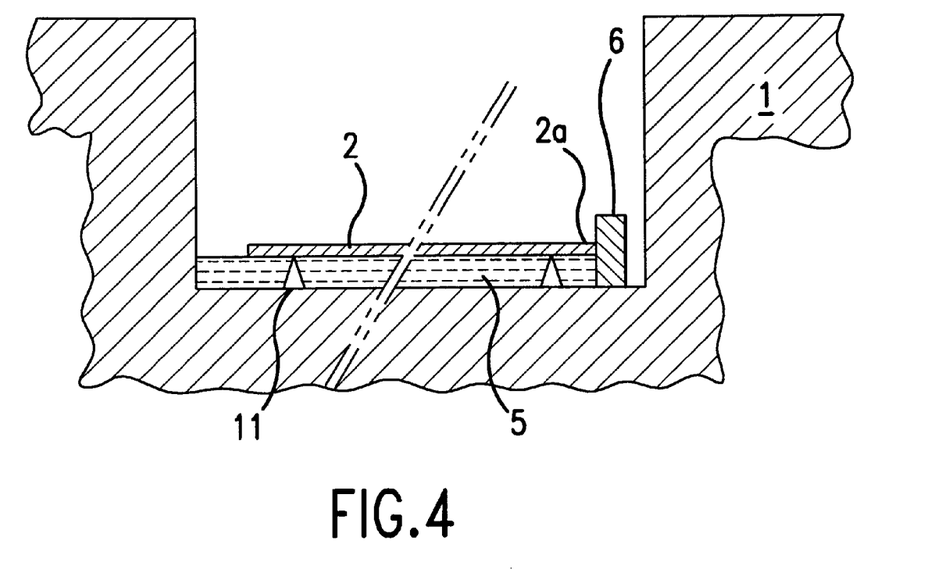
FIG. 4 represents a view on an enlarged scale of the treatment cavity of the device represented in FIGS. 2 and 3.

In FIG. 4, stops 6 for positioning the glass slide 2 are shown. Indeed, the slide is placed in contact with these stops. During immobilization of the oligonucleotides on the slide, the position of the oligonucleotides in the heat gradient is determined from the edge 2a of the slide thus coming into contact with the stop. The metal block 1 is made of stainless steel 3041 having for example a thermal conductivity of between 10 and 50 W/m.K; it is insulated by an envelope 7 having an intrinsic conductivity, for example, of less than 0.06 W/m.K, for example made of polyurethane.

The ends of the device were connected to water baths affording circulation of the cold and hot sources whose thermal regulation is stable at ±0.02° C. according to the recommendations of the manufacturer (cryothermostat ministat Huber, −25/+120° C.).

Figure 5:
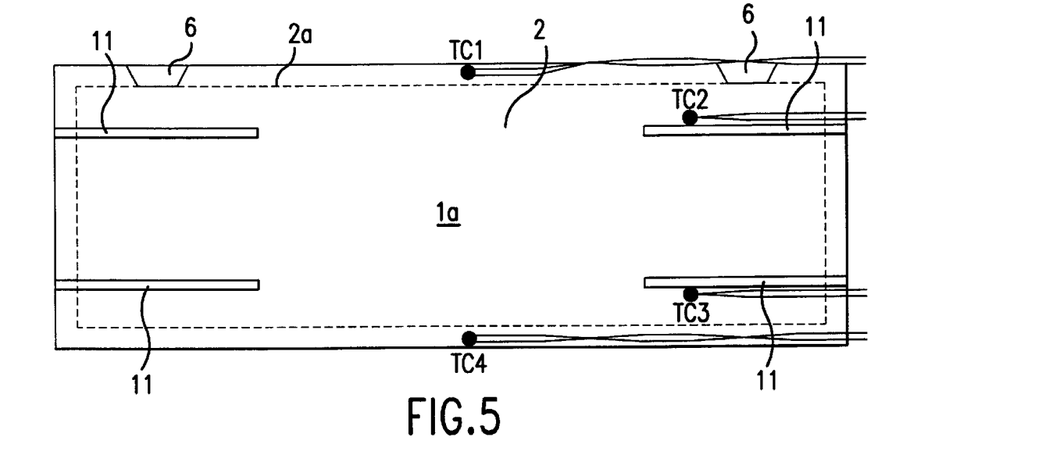
FIG. 5 represents a top view of the device represented in FIGS. 2 and 3, limited to the treatment and measuring cavity, instrumented.

The temperatures of the device were controlled by means of the chromel-alumel thermocouples (type K) described in FIG. 5. The thermocouples TCI [sic] and TC4 are situated on either side of the slide 2, whereas the thermocouples TC2 and TC3, whose wires have a total diameter of 0.08 mm; are situated under the glass slide, in the hybridization solution. These thermocouples were electrically welded directly onto the steel. Their positions (median between the two wires of the thermocouples) were determined to within 0.02 mm by means of a binocular lens overhanging a micrometric table x,y. They are differentially mounted with a cold junction dipping in an ice-cold pure water bath. The differential voltages are measured by means of a high-precision multimeter (Keithley, model 2000. Precision: 0.1 $\mu$V), and converted to temperatures by means of the standard table for these thermocouples.

The dimensions of the treatment device described above is shown by the lettered marks in FIG. 2 and is: AA:40 mm, BB:40 mm, CC:20 mm, DD:15 mm, JJ:120 mm, EE:10 mm, FF:10 mm, GG:20 mm, HH:40 mm, II:12 mm.

The linearity of the heat gradient, predicted by the numerical simulations, was experimentally checked by means of thermocouples based in the assembly. The gradient being linear, the temperatures at any point of the useful zone of the slide 2 can be simply calculated from the temperatures given by the thermocouples TC2 and TC3.

The temperature measurements which were made for several temperatures of the hot and cold sources, and at different times, show that the distribution of the temperatures is reproducible from one test to another, to within 0.1° C.

In most of the experiments reported here, the cold water bath was regulated at −9° C., and the hot water bath at +61° C. The liquid of the cold source 3 was glycol-containing water (25% glycol), and that of the hot source 2 pure water. The gradient established was 1.085° C./mm. The two edges of the glass slide, 25 mm apart, were at 13.2 and 40.3° C. respectively.

2.2—Positioning of the oligonucleotides at their predetermined optimum hybridization temperature The results of the isothermal hybridizations show that the hybridization temperature for each oligonucleotide should be sufficiently hot for there to be proper discrimination between the external mismatches. However, this temperature should remain at the same time sufficiently low for the hybridization signal to be detectable. With the device described above, the hybridization temperature is set such that the hybridization signal is equal to 25% of the hybridization signal obtained at 4° C., which corresponds to the saturation of the immobilized oligonucleotides. The position and the distribution of the the glass slide 2 (flat support), are thus roughly determined.

Figure 6:
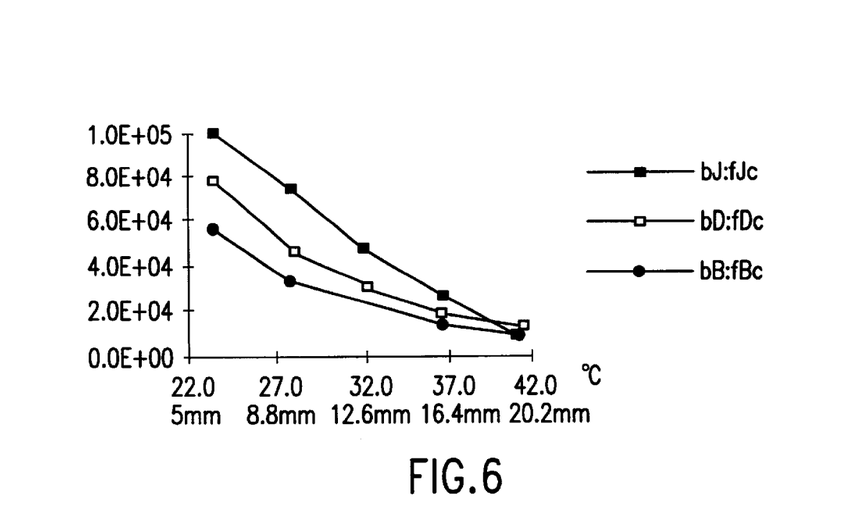
FIG. 6 represents the variation in the observed variable (fluorescence) as a function of the temperature for different nucleic fragment/oligonucleotide complexes identified in the legend placed on the right of this figure.

To refine the respective positions of the oligonucleotides in the gradient, slides were produced which carried oligonucleotides in quintuplets in the direction of the gradient. The 5 coupling sites of a quintuplet are 5, 8.8, 12.6, 16.4 and 20.2 mm respectively from the cold edge 2a of the slide 2. These slides were then hybridized with various combinations of complementary fluorescent oligonucleotides. FIG. 6 is the result of such a hybridization with the oligonucleotides fBc, fDc, and fjc. In this experiment, the water baths for the heat gradient were set at −9 and +71° C.

At the end of a few experiments of this type, the locations of the coupling sites of the different oligonucleotides respectively were defined:
bA:23.5° C.; bB:23° C.; bD:26.5° C.; bG:27.5° C.; bI:27.5° C.; bJ:29° C.

2.3—Results of hybridization in a heat gradient, according to the invention

Figure 7:
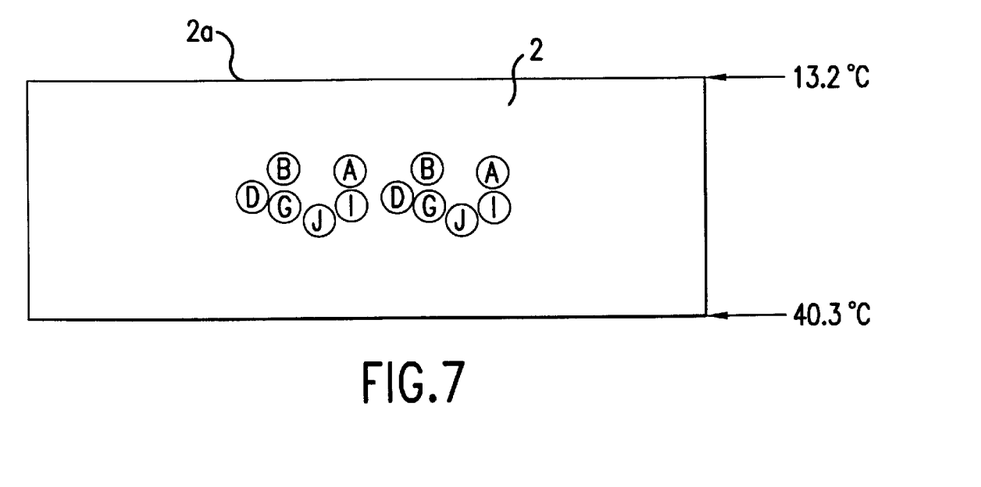
FIG. 7 represents, for a plural complexing support plate adapted to the cavity of the device according to FIGS. 2 and 3, and more particularly represented in FIG. 4, the arrangement along the width or height of this plate, but also along its length, of the coupling sites as a function of the oligonucleotides chosen.

For these experiments, the oligonucleotides bA, bB, bD, bG, bI and bJ were immobilized on glass slides 9.5, 9, 12.2, 13.2, 13.2 and 14.6 mm respectively from the cold edge 2a of the slide 2. When the water baths of the cold and hot sources are set at −9 and +61° C., these positions correspond to the temperatures defined above. The oligonucleotides were deposited in duplicate, according to the diagram in FIG. 7. The slides 2 were then hybridized in a heat gradient with the same mixture of oligonucleotides fBc, fDc and fJc used above in the isothermal hybridizations.

Figure 8:
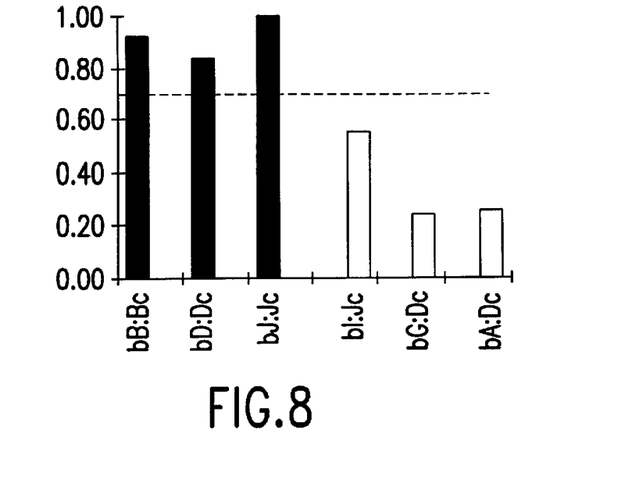
FIG. 8 represents, with the same conventions as in the abovementioned figures, the hybridization obtained with the nucleic fragments and oligonucleotides identified on the x-axes, and this with a plural complexing support according to the invention.

The hybridization results obtained are summarized in FIG. 8. They are the mean values obtained for 5 determinations. The results are expressed as relative intensity of the hybridization bJ:fjc, as for the results presented in FIGS. 1a to 1d.

It can be noted that the three perfect pairings generate a hybridization signal of comparable intensity (from 0.84 to 1), whereas the external mismatches give significantly weaker signals. In contrast to the results obtained in isothermal hybridization, it is possible here to define an intensity threshold which separates the perfect pairings from the mismatches, for example a threshold of 0.7.

In order to check the correct operation of the device described above, identical slides were hybridized with other combinations of the fluorescent oligonucleotides fAc, fBc, fDc, fGc, fIc and fJc. These combinations systematically comprised the oligonucleotide fBc. They comprised, in addition, fIc or fJc, and fAc, or fDc, or fGc. In this manner, the three fluorescent oligonucleotides of each combination did not interfere in their hybridizations because they never paired with the same fixed oligonucleotide. A combination containing fAc, fGc and fIc was also used. Indeed, cross-hybridizations between the sequences A and G are very low (see results below).

The results of these hybridizations are reported in Table 2. They were expressed relative to the intensity of the hybridization signal for the duplex bB:fBc. Furthermore, for the mismatches, the results were also expressed relative to the intensity of the hybridization signal for the corresponding perfect pairing.

These results clearly show that all the perfect pairings generate similar intensity signals. However, the pairing bG:fGc generates a signal which is slightly too weak since it is 0.79 with a standard deviation, for 6 determinations, of 0.22. The probability that the true signal, apart from the experimental variations, is effectively smaller than 1 is therefore high, about 97%. This therefore means that the position of G in the heat gradient is a little hot in these experiments, and that G can be repositioned toward the cold source.

Moreover, these results also show that the external mismatches generate signals which are considerably weaker than the perfect duplex bB:fBc, or than their respective perfect homologs. As in the specific case of hybridizations with the combination fBc+fDc+fjc, a threshold of 0.7 compared with a perfect reference duplex makes it possible to distinguish the perfect pairings from the external mismatches.

New experiments were then carried out with slides on which the oligonucleotide bG was positioned at 26.8° C. (12.5 mm from the cold edge 2a of the slide 2), the position of the other oligonucleotides remaining unchanged. These slides were hybridized with the combinations of fluorescent oligonucleotides fBc+fGc+fIc and fBc+fGc+fJc. The mean of the hybridization signal for the duplex bG:fGc compared with the duplex bB:fBc was then 1.08 on 7 determinations, with a standard deviation of 0.32. The signals for the mismatches bG:fDc and bG:fAc were then extrapolated to this new temperature for bG by taking the old values and by multiplying them with the ratio 1.08:0.79=1.367. Likewise, the signals for the mismatches bD:fGc and bA:fGc compared with their corresponding perfect homolog bG:fGc were deduced from the preceding values by dividing them by 1.367. All these results and calculations are given in Table 3.

As expected, these new results confirm and improve the preceding ones. All the perfect pairings generate a hybridization signal close to 1, whereas the terminal mismatches generate signals less than 0.5, except bI:fjc which is slightly greater. A threshold of 0.7 makes it possible to indisputably distinguish the perfect pairings from the external mismatches.

2.4—Application to the operation of a universal oligonucleotide biochip

During the use of an oligonucleotide biochip carrying, for example, all the 65 536 possible octamers, it is not very effective to simply apply an intensity threshold in order to determine if a signal is positive or negative. Indeed, the signals for the mismatches which were the most stable being only twice as weak as the signals for the perfect pairings, it is probable that experimental variations will cause a number of perfect pairings to be detected as negative, and that likewise, a number of external mismatches will be determined as positive. For example, on the entire data summarized in Table 3, there are 2 signals for perfect pairings out of the 39 reported, which are below the threshold of 0.7 (5.1%), and there are 2 of the 56 (3.6%) determinations of external mismatches which are above this threshold of 0.7. This is a value for the duplex bJ:fIc, and a value for the duplex bJ:fIc. These two duplexes form part of the three most stable mismatched duplexes of the experiments carried out.

A more effective way of proceeding is to combine all the oligonucleotides differing only by their terminal nucleotides in the same group (16 octamers for a biochip carrying all the possible octamers), and to determine, for each group, the most intense signal. It is then easy to distinguish the positive groups from the negative groups, because that will involve distinguishing the perfect pairings and the internal mismatches. For example, a threshold of 0.4 is applied in relation to the most intense signals.

Next, for each group of oligonucleotides, it is possible to apply the threshold of 0.7 in relation to the most intense signal.

If the procedure is carried out in this manner on all the experiments reported in Table 3, no perfect pairing is determined as being negative because they are all widely above the threshold of 0.4 in relation to the most intense signal of the experiment. On the other hand, the two values which were falsely determined as being positive remain falsely positive.

By applying these data, a universal oligonucleotide biochip operating in this manner would therefore have a false negative rate of 0%, a false positive rate for the internal mismatches of 0%, and a false positive rate for the extemes [sic] mismatches of 3 to 4%, which in fact corresponds to a false positive rate of about 10% for 30 and 40% of the external mismatches. Such false positive and false negative rates represent a considerable improvement of the state of the art proceeding by isothermal hybridization. Such rates are sufficiently low to allow the reconstruction of the sequence of a nucleic sample by sequencing by hybridization. Indeed, the remaining hybridization errors can be corrected by a suitable data processing software by virtue of the redundancy of the hybridizations (5).

To further improve the quality of the results, it will be possible to carry out two hybridization experiments per sample instead of only one. The false positive rate should then be of the order of 1% for 30 to 40% of the external mismatches.

TABLE 1

| Oligonucleotides | Hybridization |
| --- | --- |
| bA:fDc | 0.31 |
| bB:fBc | 0.86 |
| bC:fBc | 0.06 |
| bD:fDc | 0.73 |
| bE:fDc | 0.02 |
| bF:fBc | 0.14 |
| bG;fDc | 1.03 |
| bH:fJc | 0.14 |
| bI:fJc | 0.79 |
| bJ:fJc | 1.00 |

TABLE 2

Results of the hybridizations in a heat gradient

Intensities relative to the perfect pairings in relation to bB:fBc

| Duplex | Temperature (1) | Mean (2) | n (3) | Standard deviation |
| --- | --- | --- | --- | --- |
| bA:fAc | 23.5 | 0.99 | 6 | 0.13 |
| bD:fDc | 26.5 | 1.01 | 7 | 0.28 |
| bG:fGc | 27.5 | 0.79 | 6 | 0.22 |
| bI:fIc | 27.5 | 1.08 | 10 | 0.36 |
| bJ:fJc | 29 | 1.06 | 9 | 0.31 |
| Total | | | 38 | |

Discrimination of the external mismatches

| Duplex | Temperature (1) | n (3) | Mean (2) | Standard Deviation |
| --- | --- | --- | --- | --- |

In relation to the duplex bB:fBc

| bI:fJc | 27.5 | 9 | 0.56 | 0.14 |
| bJ:fIc | 29 | 10 | 0.44 | 0.18 |
| bG:fDc | 27.5 | 6 | 0.27 | 0.07 |
| bD:fAc | 26.5 | 6 | 0.46 | 0.22 |
| bD:fGc | 26.5 | 6 | 0.25 | 0.19 |
| bA:fDc | 23.5 | 7 | 0.25 | 0.18 |
| bA:fGc | 23.5 | 6 | 0.00 | 0.10 |
| bG:fAc | 27.5 | 4 | 0.15 | 0.06 |
| Total | | 54 | | |

| Duplex | Temperature (1) | n (3) | Mean (4) | Standard Deviation |
| --- | --- | --- | --- | --- |

In relation to the perfect duplex (4)

| bI:fJc | 27.5 | 9 | 0.54 | 0.12 |
| bJ:fIc | 29 | 12 | 0.42 | 0.16 |
| bG:fDc | 27.5 | 6 | 0.28 | 0.12 |
| bD:fAc | 26.5 | 6 | 0.46 | 0.18 |
| bD:fGc | 26.5 | 6 | 0.29 | 0.19 |
| bA:fDc | 23.5 | 7 | 0.30 | 0.23 |
| bA:fGc | 23.5 | 6 | −0.01 | 0.10 |
| bG:fAc | 27.5 | 4 | 0.15 | 0.06 |
| Total | | 56 | | |

(1) bB:fBc is at 23° C.
(2) Mean of the ratios (duplex/bB:fBc)
(3) Number of determinations
(4) Mean of the ratios (duplex/perfect duplex for the fluorescent oligonucleotide)

TABLE 3

Results of the hybridizations in a heat gradient bG positioned at 26.8° C.

Intensities relative to the perfect pairings in relation to bB:fBc

| Duplex | Temperature (1) | Mean (2) | n (3) | Standard deviation |
| --- | --- | --- | --- | --- |
| bA:fAc | 23.5 | 0.99 | 6 | 0.13 |
| bD:fDc | 26.5 | 1.01 | 7 | 0.28 |
| bG:fGc | 26.8 | 1.08 | 7 | 0.32 |
| bI:fIc | 27.5 | 1.08 | 10 | 0.36 |
| bJ:fJc | 29 | 1.06 | 9 | 0.31 |
| Total | | | 39 | |

Discrimination of the external mismatches

| Duplex | Temperature (1) | n (3) | Mean (2) | Standard deviation |
| --- | --- | --- | --- | --- |

In relation to the duplex bB:fBc

| bI:fJc | 27.5 | 9 | 0.56 | 0.14 |
| bJ:fIc | 29 | 10 | 0.44 | 0.18 |

TABLE 3-continued

Results of the hybridizations in a heat gradient bG positioned at 26.8° C.

| bG:fDc (5) | 26.8 | 6 | 0.37 | 0.07 |
|---|---|---|---|---|
| bD:fAc | 26.5 | 6 | 0.46 | 0.22 |
| bD:fGc (6) | 26.5 | 6 | 0.25 | 0.19 |
| bA:fDc | 23.5 | 7 | 0.25 | 0.18 |
| bA:fGc (6) | 23.5 | 6 | 0.00 | 0.10 |
| bG:fAc (5) | 26.8 | 4 | 0.21 | 0.06 |
| Total | | 54 | | |

| Duplex | Temperature (1) | n (3) | Mean (4) | Standard deviation |
|---|---|---|---|---|
| In relation to the perfect duplex (4) | | | | |
| bI:fJc | 27.5 | 9 | 0.54 | 0.12 |
| bJ:fIc | 29 | 12 | 0.42 | 0.16 |
| bG:fDc (5) | 26.8 | 6 | 0.38 | 0.12 |
| bD:fAc | 26.5 | 6 | 0.46 | 0.18 |
| bD:fGc (6) | 26.5 | 6 | 0.21 | 0.19 |
| bA:fDc | 23.5 | 7 | 0.30 | 0.23 |
| bA:fGc (6) | 23.5 | 6 | 0.00 | 0.10 |
| bG:fAc (5) | 26.8 | 4 | 0.21 | 0.06 |
| Total | | 56 | | |

(1) bB:fBc is at 23° C.
(2) Mean of the ratios (duplex/bB:fBc)
(3) Number of determinations
(4) Mean of the ratios (duplex/perfect duplex for the fluorescent oligonucleotide
(5) Mean values calculated by multiplying the values in Table 2 by 1.367. n and standard deviation left unchanged.
(6) For the ratio of the perfect duplex, mean value calculated by dividing the value in Table 2 by 0.367. n and standard deviation left unchanged.

Bibliographic references incorporated into the present description as required (1) K. R. Khrapko, Y. P. Lysov, A. A. Khorlyn, V. V. Shick, V. L. Florentiev and A. D. Mirzabekov; An oligonucleotide hybridization approach to DNA sequencing; FEBS Letters; 1989; 256, 118–122.
(2) M. J. Doktycz, M. D. Morris, S. J. Dormady, K. L. Beattie and K. B. Jacobson; Optical melting of 128 octamer DNA duplexes; J. Biol. Chem.; 1995; 270; 8439–8445.
(3) K. J. Breslauer, R. Frank, H. Blocker and L. A. Mary; Predicting DNA duplex stabilite [sic] from the base sequence; Proc. Natl. Acad. Sci. USA; 1986; 83; 3746–3750.
(4) U. Maskos and E. M. Southern; A study of oligonucleotide reassociation using large arrays of oligonucleotides synthesized on a glass support; Nucleic Acids Research; 1993; 21; 4663–4669.
(5) Z. Strezoska, T. Paunesku, D. Radosavljevic, 1. [sic] Labat, R. Drmanac and R. Crkvenjak-ov; DNA sequencing by hybridization: 100 bases read by a non-gel-based method; Proc. Natl. Acad. Sci. USA; 1991; 88; 10089–10093.
(6) E. M. Southern et al. (1992); Analyzing and comparing nucleic acid sequences by hybridization to arrays of oligonucleotides; evaluation using experimental models. Genomics 13, 1008–1017.
(7) R. Drmanac et al. (1993); DNA sequence determination by hybriization [sic] a strategy for efficient large-scale sequencing. Science 260; 1649–1652.
(8) Carrano et al. (1989); A high resolution, fluorescence based, semi-automated method for DNA fingerprinting, Genomic 4, 129–136.
(9) Lysov, Yu et al. (1988); Doklady akademi. Nauk. SSR 303: 1508–1511.
(10) Drmanac, R. et al. (1989) Genomics 4: 114–128.
(11) Sze VLSI Technology, McGraw Hill 1983.

What is claimed is:

1. A method for simultaneously hybridizing in a liquid medium a plurality of different nucleic ligands each in the free state in said liquid medium, said ligands belonging to a same component or several components in the free state in said liquid medium, said method comprising:
   a) providing a same support for plural hybridization on which there are distributed a plurality of immobilizing sites, separated from each other;
   b) temperature conditioning said support so as to have different local temperature values respectively in said immobilizing sites, at least along one reference direction of said support;
   c) providing a plurality of different nucleic anti-ligands capable of specifically hybridizing respectively with nucleic ligands;
   d) determining for each of said anti-ligands the optimum temperature value at which the corresponding ligand/anti-ligand complex is stable;
   e) distributing and immobilizing said anti-ligands in said different immobilizing sites, so as to substantially match said local temperature values with said optimum temperature values, as an exogenous parameter from which the stability of said ligand/anti-ligand complexes depend directly or indirectly;
   f) contacting said liquid medium with said support, with the plurality of said anti-ligands immobilized in said support; and
   g) sensing the presence and/or the quantity of the different complexes formed between said immobilized anti-ligands and corresponding ligands of the liquid medium.

2. A method according to claim 1, wherein the contacting step according to (f) is performed by applying the same minimum temperature value to all the immobilizing sites, said minimum temperature value being sufficient to hybridize practically all the ligands with the anti-ligands, and then the support is washed by applying to the different immobilizing sites local temperature values which are respectively different and predetermined.

3. A method according to claim 1, wherein the contacting step according to (f) is carried out by applying to the different immobilizing sites first local temperature values which are respectively different and predetermined, and the support is then washed by maintaining the different immobilizing sites at second local temperature values which are respectively different, the first values being identical to or different from the second values respectively of said local temperature.

4. A method according to claim 1, wherein the contacting step according to (f) is carried out by applying to the different immobilizing sites local temperature values which are respectively different and predetermined, and the hybridized support is washed with a washing liquid at a relatively cold and constant temperature.

5. A method according to claim 1, wherein a spatial gradation of the local temperature values is established on the support in at least one reference direction of said support.

6. A method according to claim 1, wherein the different ligand/anti-ligand complexes are sensed using at least one of labeling of the component(s) of the liquid medium and labeling of the different ligand/anti-ligand complexes immobilized on the support.

7. A method according to claim 1, wherein the liquid medium is obtained from a sample containing one or more different entities to be analyzed.

8. A method according to claim 7, wherein the sample is a biological sample.

9. A method according to claim 7, wherein the sample is subjected to at least one preliminary sample operation to obtain one or more components in the liquid medium that are identical to or derived directly from the one or more different entities respectively and that are representative of said one or more different entities.

10. A method according to claim 1, wherein the support onto which the different ligands are immobilized is subjected to at least one subsequent operation in order to separate from said support the component(s) which have not been coupled and/or to elute or release the different ligands differentially or otherwise.

11. A method according to claim 1, wherein the liquid medium comprises several different components comprising nucleic ligands which are respectively different, whereby said different components are hybridized and separated from each other on said support.

12. A method according to claim 11, wherein said method is carried out in at least one application selected from the group consisting of identification, quantification, separation and fractionation of said different components.

13. A method according to claim 1, wherein the liquid medium contains a single component in the liquid medium, said single component comprising or exhibiting several nucleic ligands which are respectively different, whereby the single component is hybridized with different anti-ligands, respectively.

14. A method according to claims 13, wherein the single component is a nucleic acid in which the succession of nucleotides of at least one strand determines a plurality of hybridization regions, and therefore of ligands, according to the target nucleotide sequences, which are respectively complementary to the probe nucleotide sequences of the anti-ligands.

15. A method according to claim 14, wherein said method is carried out in at least one application selected from the group consisting of sequencing by hybridization of the nucleic component of the liquid medium, resequencing of the nucleic component, analysis and identification of a nucleic material or sample, and typing of a nucleic material.

16. A method according to claim 7, wherein the liquid medium is obtained from a nucleic sample comprising one and the same fragment, or several different nucleic fragments.

17. A method according to claim 16, wherein the nucleic sample is subjected to at least one preliminary operation selected from the group consisting of denaturation, cloning and amplification.

18. A method according to claim 1, wherein liquid medium is contacted with said support after it has been temperature conditioned.

19. A device for simultaneously hybridizing in a liquid medium a plurality of different nucleic ligands each in the free state in said liquid medium, said ligands belonging to a same component or several components in the free state in said liquid medium, comprising:
   a) a same support for plural hybridization on which there are distributed a plurality of immobilizing sites, separated from each other;
   b) temperature conditioning means for said support so as to have in working conditions different local temperature values respectively in said immobilizing sites, at least along one reference direction of said support;
   c) a plurality of different nucleic anti-ligands capable of specifically hybridizing respectively with nucleic ligands, said anti-ligands being distributed and immobilized in said different immobilizing sites, so as to substantially match in working conditions the different local temperature values in said immobilizing sites with the different optimum temperature values at which the corresponding ligand/anti-ligand complexes are stable;
   d) means for contacting said liquid medium with said support; and
   e) means for detecting the different complexes formed between said immobilized anti-ligands and corresponding ligands of the contacted liquid medium.

* * * * *